United States Patent [19]

Hamprecht et al.

[11] 4,049,709
[45] Sept. 20, 1977

[54] VINYL-SUBSTITUTED SULFAMIC ACID HALIDES

[75] Inventors: Gerhard Hamprecht, Mannheim; Siegfried Kersten, Ludwigshafen, both of Germany

[73] Assignee: BASF Aktiengesellschaft, Ludwigshafen, Germany

[21] Appl. No.: 735,218

[22] Filed: Oct. 22, 1976

[30] Foreign Application Priority Data

Nov. 28, 1975 Germany ............................ 2553461

[51] Int. Cl.$^2$ ............................................. C07C 143/86
[52] U.S. Cl. ................................................ 260/543 R
[58] Field of Search ........................ 260/543 R, 513.6

[56] References Cited

U.S. PATENT DOCUMENTS

3,992,444  11/1976  Hamprecht et al. ............. 260/543 R

FOREIGN PATENT DOCUMENTS

| 1,085,980 | 8/1954 | France | 260/543 R |
| 1,121,060 | 1/1962 | Germany | 260/543 R |
| 2,401,819 | 7/1975 | Germany | 260/543 R |

*Primary Examiner*—Norman Morgenstern
*Attorney, Agent, or Firm*—Keil, Thompson & Shurtleff

[57] ABSTRACT

New sulfamic acid halides and a process for the manufacture of sulfamic acid halides by reacting sulfamic acids with aldehydes and acid halides. The products are starting materials for the manufacture of crop protection agents, dyes and pharmaceuticals.

4 Claims, No Drawings

VINYL-SUBSTITUTED SULFAMIC ACID HALIDES

The invention relates to new sulfamic acid halides and to a process for the manufacture of sulfamic acid halides by reacting sulfamic acids with aldehydes and acid halides.

The manufacture of N-alkylamidosulfonyl chlorides by reacting monoalkylammonium chlorides with sulfuryl chloride has been disclosed (Acta. Chem. Scand. 17 (1963), 2141). When the reaction is carried out in the presence of a strongly polar, organic solvent, with the addition of a metal halide as the catalyst, the yields are improved (German Pat. No. 1,242,627). Whilst the process gives good yields in the case of lower, non-branched alkylamidosulfonyl chlorides, the yields decrease substantially if the alkyl radical is branched, and as its chain length is increased. The above method also cannot be used to manufacture haloalkylaminosulfonyl halides. A further disadvantage is the long reaction time which the process requires in order to give a satisfactory yield. In industrial operation, particularly, these processes present difficulties in working up, including environmental problems, due to the high chlorine content of the by-products. German Laid-Open Application No. 1,943,233 discloses a process for the manufacture of β-chloroethylaminosulfonyl fluoride by halogen exchange of the corresponding aminosulfonyl chloride with hydrogen fluoride, under superatmospheric pressure. Bearing in mind the reaction conditions required, and the fact that the reaction is carried out in two stages, via the sulfonyl chloride first produced, the process is unsatisfactory from the point of view of simple and economical operation, particularly on an industrial scale.

The manufacture of N,N-dimethylaminosulfonyl chloride by reacting sulfuryl chloride with diemthylamine has been disclosed (Chemische Berichte, 14 (1881), 1,810–1,812). Particularly on an industrial scale, the process is involved and uneconomical, and gives unsatisfactory yields. N-Haloalkyl compounds cannot be manufactured by this method.

German Published Application DAS No. 1,028,129 discloses the manufacture of N,N-dialkylsulfamic acid chlorides by reacting secondary N-chloramines with sulfur dioxide. The manufacture of such sulfuric acid chlorides by reacting dialkylcarbamic acid chlorides with sulfur trioxide has also been disclosed (German Pat. No. 946,710). However, substituted alkyl derivatives are not obtainable by either process. Whilst the reaction of N-chloro-N,N-dialkylamines with sulfur dioxide is difficult to carry out industrially because the chloramines tend to decompose abruptly, the reaction of sulfur trioxide with dialkylcarbamic acid chlorides can only be used in the case of unsubstituted acid chloride starting materials of a low number of carbon atoms, because of the powerful oxidizing action of the sulfur trioxide.

It is an object of the present invention to provide a new process whereby hitherto inaccessible N-disubstituted sulfamic acid halides can be manufactured simply and economically, and in high yield and purity.

It is a further object of the present invention to provide the new sulfamic acid halides.

We have found that these objects are achieved and that sulfamic acid halides of the formula

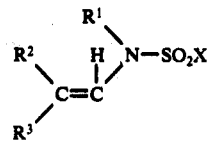
I where $R^1$ is an alipatic or cycloaliphatic radical, $R^2$ and $R^3$ may be identical or different and each is hydrogen, halogen or an aliphatic radical and X is halogen, are obtained advantageously when sulfamic acid compounds of the formula

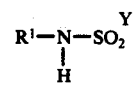
II where $R^1$ has the above meanings and Y is hydroxyl or halogen, are reacted with aldehydes of the formula

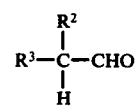
III where $R^2$ and $R^3$ have the above meanings, and an acid halide of phosphoric acid, or phosphorous acid or of carbonic acid, thionyl chloride, sulfur tetrafluoride and/or sulfur dichloride.

Further, we have found that the resulting sulfamic acid halides of the formula

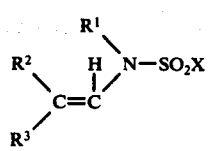
I where $R^1$ is an aliphatic or cycloaliphatic radical, $R^2$ and $R^3$ may be identical or different and each is hydrogen, halogen or an aliphatic radical and X is hydrogen, can advantageously be reacted with a hydrogen halide to give the sulfamic acid halides of the formula

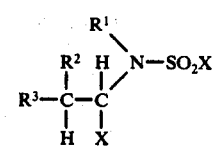
IV where $R^1$, $R^2$, $R^3$ and X have the above meanings.

Further, we have found the new sulfamic acid halides of the formula

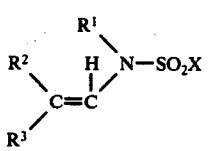
I where $R^1$ is an aliphatic or cycloaliphatic radical, $R^2$ and $R^3$ may be identical or different and each is hydrogen, halogen or an aliphatic radical, and X is halogen.

Preferred end products I we have found are the new sulfamic acid halides of the formula

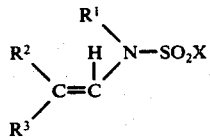

I where $R^1$ is alkyl of 1 to 20 carbon atoms, which may be unsubstituted or substituted by one or more chlorine atoms, or is cycloalkyl of 4 to 8 carbon atoms, $R^2$ and $R^3$ are identical or different and each is hydrogen, bromine, chlorine or alkyl of 1 to 18 carbon atoms and X is bromine or chlorine.

Further, we have found the new sulfamic acid halides of the formula

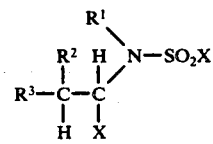

IV where $R^1$ is an aliphatic or cycloaliphatic radical, $R^2$ and $R^3$ are identical or different and each is hydrogen, halogen or an aliphatic radical, and each X is halogen and where, if $R^2$ and $R^3$ are simultaneously each hydrogen and/or halogen, or $R^2$ is hydrogen and $R^3$ is alkyol of 1 to 18 carbon atoms, or alkoxyalkyl of 2 to 18 carbon atoms, which may each be unsubstituted or substituted by chlorine, fluorine and/or carbalkoxy of 2to 5 carbon atoms, or if both $R^2$ and $R^3$ are alkyl and/or alkoxyalkyl, in which case $R^2$ and $R^3$ together contain from 2 or 4 to 18 carbon atoms and may in addition each carry chlorine, fluorine and/or carbalkoxy of 2 to 5 carbon atoms, $R^1$ is a cycloaliphatic radical or is an aliphatic radical which is not substituted by halogen atoms, or which is substituted by one or more halogen atoms at the carbon atom in the α-position, γ-position and/or even more remote positions relative to the nitrogen atom.

Preferred end products IV we have found are the new sulfamic acid halides of the formula

IV

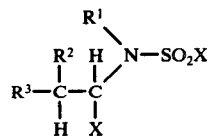

-continued where $R^1$ is alkyl of 1 to 20 carbon atoms which is unsubstituted or is substituted by one or more chlorine atoms at the carbon atom in the α-position, γ-position and/or even remote positions relative to the nitrogen atom, or is cycloalkyl of 4 to 8 carbon atoms, $R^2$ and $R^3$ are identical or different and each is hydrogen, bromine, chlorine or alkyl of 1 to 18 carbon atoms, and X is bromine or chlorine.

Where ethylsulfamic acid, ethylsulfamic acid chloride, thionyl chloride and hydrogen chloride are used, the reaction can be represented by the following equations:

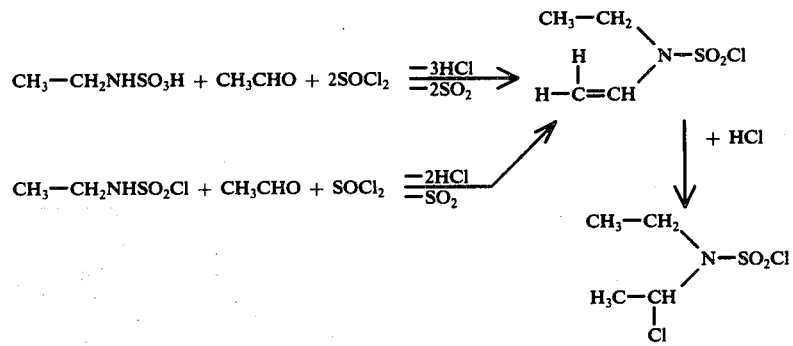

Compared to the prior art, the process of the invention provides hitherto inaccessible N-disubstituted sulfamic acid halides in a simple and economical manner, in high yield and purity. The reaction time is short and the working up of the reaction mixture — particularly with regard to protection of the environment — is simple and safe. In contrast to the acid halides mentioned, sulfuryl chloride is not a suitable reactant. Starting materials II where alkyl is of a higher number of carbon atoms can be reacted by the process of the invention. All these advantageous results are surprising in view of the prior art.

Preferred starting materials II and III are, accordingly, preferred end products I and IV are those where $R^1$ is straight or branched alkyl and haloalkyl, especially chloroalkyl or bromoalkyl, of 1to 20, especially 1 to 8, carbon atoms, or is cycloalkyl of 4 to 8 carbon atoms, $R^2$ and $R^3$ are identical or different and each is hydrogen, fluorine, or especially, bromine or chlorine, or straight or branched alkyl or haloalkyl, especially chloroalkyl or bromoalkyl, of 1to 18, especially 1 to 8, carbon atoms, X is fluorine or especially chlorine or bromine and Y is hydroxyl or fluorine or, especially, bromine or chlorine. The said radicals may additionally be substituted by groups and/or atoms which are inert under the reaction conditions, e.g. chlorine, bromine, alkyl of 1 to 4 carbon atoms or carbalkoxy of 2 to 4 carbon atoms.

Preferred starting materials II are methylsulfamic acid, ethylsulfamic acid, n-propylsulfamic acid, isopropylsulfamic acid, n-butylsulfamic acid, isobutylsulfamic acid, sec.-butylsulfamic acid, tert.-butylsulfamic acid, pentylsulfamic acid, pentyl-(3)-sulfamic acid, cyclopentylsulfamic acid, hexylsulfamic acid, cyclohexylsulfamic acid, heptylsulfamic acid, 1,2-dimethylbutylsulfamic acid, 1,3-dimethylbutylsulfamic acid, 2-chloropropylsulfamic acid, 3-chloropropylsulfamic acid, 2-chloroisopropylsulfamic acid, 1-(chloromethyl)-propyl-(1)-sulfamic acid, 2-chloro-2-methyl-propyl-(1)-sulfamic acid, tert.-amylsulfamic acid, 2-chloroethylsulfamic acid, 1-chloropropyl-(2)-sulfamic acid, 3-chlorobutyl-(4)-sulfamic acid, 1-chlorobutyl-(2)-sulfamic acid and 2-chlorobutyl-(3)-sulfamic acid and analogous sulfamic acid fluorides, sulfamic acid bromides and, especially, sulfamic acid chlorides.

Aldehydes III used advantageously are acetaldehyde, propionaldehyde, n-butylraldehyde, iso-butyraldehyde, 2-methylbutyraldehyde, 2-ethyl-caproaldehyde, n-valeraldehyde, isovaleraldehyde, isovaleraldehyde, n-caproaldehyde, 2-methyl-valeraldehyde, 3-methyl-valeraldehyde, 2-ethylbutyraldehyde, 2,2-dimethylbutyraldehyde, 2,3-dimethylbutyraldehyde, 3,3-dimethylbutyraldehyde, oenanthaldehyde, 2-methyl-caproaldehyde, 3-methyl-caproaldehyde, 4-methyl-caproaldehyde, 5-methyl-caproaldehyde, 2-ethyl-valeraldehyde, 3-ethyl-valeraldehyde, 3,3-dimethyl-valeraldehyde, 2,3-dimethyl-valeraldehyde, 4-ethyl-valeraldehyde, 4,4-dimethylvaleraldehyde, 3,4-dimethylvaleraldehyde, 2,4-dimethyl-valeraldehyde and 2-ethyl-3-methyl-butyraldehyde, and compounds which form these aldehydes, especially acetaldehyde, under the reactions conditions, in particular paraldehyde and metaldehyde, chloroacetaldehyde, dichloroacetaldehyde, bromoacetaldehyde, dibromoacetaldehyde, α-chloro-propionaldehyde, β-chloropropionaldehyde, α-bromo-propionaldehyde and β-bromo-propionaldehyde.

The starting materials II can be reacted with the starting materials III in stoichiometric amount or using an excess of material III, preferably in a ratio of from 1 to 4 moles, especially 1.1 to 1.5 moles, of starting material III per mole of starting material II. In the case of sulfamic acids with fairly long or branched chains, e.g. of at least 4 carbon atoms, suitable amounts to use are from 1.5 to 4 moles of starting material III per mole of starting material II. The starting materials II can be reacted with the acid halide in stoichiometric amount or using an excess of acid halide, preferably —depending on the starting material II— using a ratio of from 2.2 to 4 moles of acid halide per mole of sulfamic acid starting material II and from 1.1 to 2 moles of acid halide per mole of sulfamic acid halide starting material II. Preferred acid halides are thionyl chloride, phosphorus pentachloride, phosphorus trichloride, phosphorus oxchloride, phosphorus pentabromide, phosphorus tribromide, phosgene, sulfur tetrafluoride and sulfur dichloride.

As a rule, the reaction is carried out at from −40° to 120° C, especially from 10° to 100° C, under atmospheric or superatmospheric pressure, continuously or batchwise. Advantageously, solvents which are inert under the reaction conditions are used. Examples of suitable solvents are halohydrocarbons, especially chlorohydrocarbons, e.g. tetrachloroethylene, 1,1,2,2- or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentrachloroethane, o-, m- and p-difluorobenzene, 1,2-dichloroethane, 1,1,-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, nitro hydrocarbons, e.g. nitromethane, nitroethane, nitrobenzene, o-, m- and pchloronitrobenzene and o-nitrotoluene, nitriles, e.g. acetonitrile, butyronitrile, isobutyronitrile, benzonitrile and m-chlorobenzonitrile, aliphatic or cycloaliphatic hydrocarbons, e.g. heptane, pinane, nonane, o-, m- and p-cymene, gasoline fractions with boiling ranges of from 70° to 190° C, cyclohexane, methylcyclohexane, decalin, petroleum ether, hexane, naphtha, 2,2,4-trimethylpentane, 2,2,3-trimethylpentane, 2,3,3-trimethylpentane and octane, and corresponding mixtures. The amount of solvent used is advantageously from 100 to 2,000 percent by weight, preferably from 400 to 1,200 percent by weight, based on starting material II.

The reaction is suitably carried out in the presence of an acid, advantageously in the presence of from 0.5 to 10, especially from 1 to 3, moles of acid per mole of starting material II. The acids may be inorganic or organic. Instead of monobasic acids, equivalent amounts of polybasic acids may be used. Examples of suitable acids are hydrogen chloride, hydrogen bromide, hydrogen iodide, hydrogen fluoride, sulfuric acid, phosphoric acid, sulfonic acids, e.g. benzenesulfonic acid and p-toluenesulfonic acid, acids containing boron, e.g. boric acid and fluoboric acid, aliphatic carboxylic acids, e.g. chloroacetic acid, dichloroacetic acid, trichloroacetic acid, cyanoacetic acid, acetic acid, propionic acid, butyric acid and isobutyric acid, or appropriate mixtures. The acids may be used in a concentrated form, as mixtures with one another and/or as mixtures with a solvent. Hydrogen chloride, sulfuric acid, phosphoric acid and hydrogen bromide are preferred.

Lewis acid, advantageously in an amount of from 0.01 to 0.04 mole per mole of starting material III, may also be added as acids in order to accelerate the reaction. For the purposes of the invention, Lewis acids are electrophilic compounds with an incomplete electron configuration, which can take up an electron pair of a base. For a definition of Lewis acids, reference may be made to Houben-Weyl, Methoden der Organischen Chemie, Volume 4/2, page 6, and Rodd, Chemistry of Carbon Compounds, Volume IA, page 103 (Elsevier Publ. Co., N.Y. 1951). Advantageous Lewis acids to use are halides, especially chlorides, of metals of groups 2 to 6 and 8 of the periodic table, e.g. zinc chloride, boron chloride, aluminum chloride, iron chloride, tin chloride, titanium chloride, antimony chloride, bismuth chloride, molybdenum chloride, tungsten chloride, aluminum bromide and boron trifluoride. The Lewis acids may also be used in the form of their complexes, e.g. boron trifluoride etherate, fluoboric acid, boron fluoride/acetic acid, boron fluoride/diacetic acid, boron fluoride/phosphoric acid and boron trichloride complexes with phosphorus trichloride and phosphorus oxychloride. Preferred catalysts are iron(III) chloride, zinc(II) chloride and aluminum(III) chloride. In some cases it is advantageous to use a combination of the said catalysts.

The halogenation catalyst used is advantageously a carboxylic acid amide disubstituted at the nitrogen atom, a tertiary amine or a carbamic acid halide disubstituted at the nitrogen atom, especially disubstituted carbamic acid chloride, advantageously in an amount of from 0.2 to 6 percent by weight, based on starting material II. Mixtures of the said catalysts may also be used for the reaction. The amine may also be a diamine, or may be used in the form of appropriate salts, e.g. amine hydrochlorides, or quaternary salts. Preferred catalysts are trimethylamine, triethylamine, pyridine, N,N-dimethylaniline, N,N-diethylaniline, N-ethylpiperidine, N-methylpyrrolidine,$\alpha$-, $\beta$ and $\gamma$-picoline, N-propylpiperidine, quinoline, isoquinoline, quinazoline, quinoxaline, triamylamine, tri-n-butylamine, n-propyl-diisopropylamine, trifurfurylamine, trihexylamine, N-methylimidazole, N-methylpyrrole, 2,6- and 2,4-lutidine, N-(4-pyridyl)-pyridinium chloride hydrochloride, triethylenediamine, p-dimethylaminopyridine, N-dimethylcyclohexylamine, pyrimidine and acridine, dimethylformamide, diethylformamide, formic acid N-methylanilide, N,N-dimethylacetamide, N-methylpyrrolidone and tetramethylurea, dimethyl-, diethyl-, di-n-propyl-, diisopropyl-, di-n-butyl-, diisobutyl-, di-sec.-butyl-, di-tert.-butyl-, dipentyl-, di-(pentyl-2)-, di-(pentyl-3)-, di-n-hexyl-, di-n-heptyl-, di-n-octyl-, di-n-nonyl- and di-n-decyl-carbamic acid chloride, or corresponding catalyst compounds containing 2 or 3 of the above radicals which, however, are different from one another, e.g. dimethylethylamine, N-methyl-N-ethylformamide or N-methyl-N-ethylcarbamic acid chloride. At times, appropriate catalysts may also simultaneously serve as the solvent or reaction medium.

The reaction may be carried out as follows: a mixture of the starting material II, the starting material III and the halide, if appropriate together with catalyst, acid and/or solvent, is kept at the reaction temperature for from 3 to 8 hours. It is possible first to mix the halide or the starting material II with the solvent and then to add the other components. The end product I is isolated from the reaction mixture by conventional methods, as a rule by fractional distillation.

In a preferred embodiment of the process of the invention, a suspension of the sulfamic acid halide II is reacted with the aldehyde III in an inert solvent for from 2 to 30 minutes at from 10° to 40° C, and the halide is then added at from 10° to 40° C, where appropriate after first having added a catalytic amount of a halogenation catalyst. The duration and temperature of addition of the halide is advantageously selected substantially in accordance with the rate at which the gases are eliminated. In general, the acid chloride is initially added slowly. Acid halides of low boiling point, e.g. phosgene and sulfur tetrafluoride, may also be introduced as gases, at from −40° to −10° C. When the elimination of gas slows down, it is advantageous to accelerate the reaction by heating, advantageously at from 40° to 100° C, depending on the boiling point of the solvent used.

In a further advantageous embodiment of the process of the invention, the components are suspended in an inert solvent and the reaction is then assisted by adding an acid catalyst; for example, the reaction mixture is saturated with a hydrogen halide at from −20° to +60° C, the halide is then added and the reaction is carried out in the above manner.

Depending on the temperature and on the starting material III used, either only the end product I, or substantial amounts of the end product IV, are produced. It is possible first to produce the end product I in the above manner, preferably at from 70° to 100° C, using aldehydes III of up to 10 carbon atoms and starting materials II of up to 10 carbon atoms, and then slowly to isolate the said end product from the reaction mixture by distillation under reflux, advantageously in the course of from ½ to 2 hours. An addition reaction with hydrogen halide, preferably hydrogen chloride, can then be carried out in a further step, under atmospheric or superatmospheric pressure, continuously or batchwise, advantageously in the course of from 10 to 40 minutes, and advantageously in the presence of the above solvents and Lewis acids, the end product IV being obtained. The preferred conditions for the addition reaction are from 0° to 50° C, a ratio of from 1.0 to 1.2 moles of hydrogen halide per mole of end product I, and the above ratios of solvent and Lewis acid, based on end product I instead of on starting material II. The end product IV is then isolated from the addition reaction mixture by conventional methods, e.g. by distillation, preferably by molecular distillation.

In a preferred embodiment, the reaction, followed by the addition reaction with hydrogen halide, are carried out in the same vessel, the first reaction being carried out, advantageously at from 70° to 100° C in the course of from 1 to 8 hours, followed immediately, in the same vessel, by the addition reaction at from 0° to 50° C, advantageously using from 1 to 1.2 moles of hydrogen halide, preferably hydrogen chloride, per mole of end product I, with reaction times of from 10 to 40 minutes. In respect of other conditions, this conjoint reaction and addition of hydrogen halide is in general carried out in the maner described above for the first reaction alone.

The new compounds which may be manufactured by the process of the invention are valuable starting materials for the manufacture of crop protection agents, dye and pharmaceuticals. Thus, herbicides may be manufactured from the end products I of the invention by reaction with glycollic acid anilides (German Laid-Open Application DOS No. 2,351,608). Hydrolysis of the end products I may be used to produce the corresponding haloamines, which are starting materials for chemotherapeutic agents for combating cancer and tumors (Ullmanns Encyklopadie der technischen Chemie, Volume 10, pages 773 et seq.). Using the process disclosed in Arzneimittelforschung 12 (1962), 1,119 et seq. the end products I can be converted to N,N-bis-($\alpha$-haloalkyl)-sulfamyl-hydrazones, which are active against sarcomas and carcinomas. Herbicidal sulfamic acid esters may be manufactured from the end products I by reaction with 2-alkoxy-2,3-dihydro-3,3-dimethyl5-hydroxy-benzofuran derivatives (German Laid-Open Application DOS No. 2,324,592).

In the context of the uses enumerated, new end products I and IV to be used advantageously are the sulfamic acid halides I and IV described above as being preferred, especially N-methyl-N-$\alpha$-chloroethyl sulfamic acid chloride, N-ethyl-N-$\alpha$-chloroethyl sulfamic acid chloride, N-methyl-N-vinylsulfamic acid chloride and N-ethyl-N-vinylsulfamic acid chloride.

In the Examples which follow, parts are by weight.

EXAMPLE 1 a. 129.4 parts of methylsulfamic acid chloride and 152 parts of paraldehyde in 620 parts of 1,2-dichloroethane are mixed for 5 minutes at room temperature. After adding 0.1 part of $\alpha$-picoline, 162 parts of thionyl chloride are added whilst stirring and the reaction mixture is heated up slowly, being stirred for 2 hours at 50° C and one hour at 83° C. After concentrating the mixture under reduced pressure, distillation gives 148 parts of a mixture of 66 percent by weight of N-α-chloroethyl-N-methylsulfamic acid chloride and 34 percent by weight of N-methyl-N-vinylsulfamic acid chloride (83% of theory), of boiling point 72°-79° C/0.6 mm Hg and $n_D^{25}$ = 1.4780.

b. 10 parts of the reaction mixture obtained, in 50 parts of 1,2-dichloroethane, are saturated with hydrogen chloride at room temperature, in the presence of 0.07 part of aluminum-(III) chloride, whilst stirring. After concentrating the mixture at 50° C/11 mm Hg, 10.9 parts of N-α-chloroethyl-N-methylsulfamic acid chloride (100% of theory) of $n_D^{25}$ = 1.4822 are obtained.

EXAMPLE 2

143.5 parts of ethylsulfamic acid chloride and 110 parts of paraldehyde in 500 parts of 1,2-dichloroethane are saturated with hydrogen chloride whilst stirring at 40° C. The reaction mixture is cooled to 15° C, and 0.2 part of pyridine are added, followed by 155 parts of thionyl chloride added in the course of 15 minutes. The reaction mixture is stirred for one hour at 25° C and is then slowly heated to the reflux temperature. After stirring for 4 hours, the mixture is concentrated under reduced pressure and the residue is distilled. 104 parts of a mixture of 75 percent by weight of N-α-chloroethyl-N-ethylsulfamic acid chloride and 25 percent by weight of N-ethyl-N-vinylaminosulfonyl chloride (53% of theory), of boiling point 69°-72° C/0.04 mm Hg and $n_D^{25}$ = 1.475 are obtained.

We claim:
1. Sulfamic acid halides of the formula

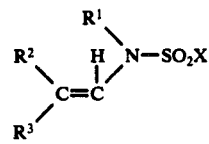

where $R^1$ is an aliphatic or cycloaliphatic radical, $R^2$ and $R^3$ may be identical or different and each is hydrogen, halogen or an aliphatic radical and X is halogen.

2. Sulfamic acid halides of the formula

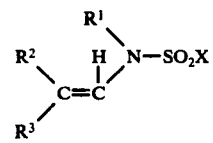

where $R^1$ is an alkyl of 1 to 20 carbon atoms, which may be unsubstituted or substituted by one or more chlorine atoms, or is cycloalkyl of 4 to 8 carbon atoms, $R^2$ and $R^3$ may be identical or different and each is hydrogen, bromine, chlorine or alkyl of 1 to 18 carbon atoms, and X is bromine or chlorine.

3. N-Methyl-N-vinylsulfamic acid chloride.
4. N-Ethyl-N-vinylsulfamic acid chloride.

* * * * *